US006281223B1

(12) United States Patent
Choy et al.

(10) Patent No.: US 6,281,223 B1
(45) Date of Patent: *Aug. 28, 2001

(54) RADIOENHANCED CAMPTOTHECIN DERIVATIVE CANCER TREATMENTS

(75) Inventors: Hak Choy, Nashville, TN (US); Luigi Lenaz, Newtown, PA (US)

(73) Assignee: SuperGen, Inc., Dublin, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/290,446

(22) Filed: Apr. 13, 1999

(51) Int. Cl.$^7$ .................................................. A61K 31/44
(52) U.S. Cl. ............................................................ 514/283
(58) Field of Search ............................................. 514/283

(56) References Cited

FOREIGN PATENT DOCUMENTS

| WO 99/15153 | 1/1999 | (WO) | ............................. A61K/9/127 |
| WO 99/06031 | 11/1999 | (WO) | ............................... A61K/9/64 |

OTHER PUBLICATIONS

McLemore et al., Comparison of Intrapulmonary, Percutaneous Intrathoracic, and Subcutaneous Models for the Propagation of Human Pulmonary and Nonpulmonary Cancer Cell Lines in Athymic Nude Mice, Cancer Research 48, May 15, 1988, pp. 2880–2886.

Jaxel et al., Structure–Activity Study of the Actions of Camptothecin Derivatives On Mammalian Topoisomerase I: Evidence for a Specific Receptor Site and a Relation to Antitumor Activity, Cancer Research 49, Mar. 15, 1989, pp. 1465–1469.

Hsiang et al., Arrest of Replication Forks by Drug–Stabilized Topoisomerase I–DNA Cleavable Complexes as a Mechanism of Cell Killing by Camptothecin, Cancer Research 49, Sep. 15, 1989, pp. 5077–5082.

Musk et al., The inhibition of cellular recovery in human tumour cells by inhibitors of topoisomerase, Br. J. Cancer, 62, 1990, pp. 365–367.

Kim et al., Potentiation Of Radiation Response In Human Carcinoma Cells In Vitro And Murine Fibrosarcoma In Vivo By Topetecan, An Inhibitor of DNA Topoisomerase I, Int. J. Radiation Oncology Biol. Phys., vol. 22, Jul. 3, 1991, pp. 515–518.

Mattern, et al. Synergistic Cell Killing by Ionizing Radiation and Topoisomerase I Inhibitor Topotecan (SK&F 104864), Cancer Research 51, Nov. 1, 1991, pp. 5813–5816.

Boothman et al., Posttreatment Exposure To Camptothecin Enhances The Lethal Effects of X–Rays On Radioresistant Human Malignant Melanoma Cells, Int. J. Radiation Oncology Biol. Phys. vol. 24, No. 5, Jun. 1992, pp. 939–948.

Pantazis, et al., Cytotoxic Efficacy of 9–Nitrocamptothecin in the Treatment of Human Malignant Melanoma Cells in Vitro, Cancer Research 54, Feb. 1, 1994, pp. 771–776.

Hennequin et al., Interaction of Ionizing Radiation with the Topisomerase I Poison Camptothecin in Growing V–79 and HeLa Cells, Cancer Research 54, Apr. 1, 1994, pp. 1720–1728.

Hinz et al., Pharmacokinetics of the in Vivo and in Vitro Conversion of 9–Nitro–20(S)–camptothecin to 9–Amino–20(S)–camptothecin in Humans, Dogs, and Mice, Cancer Research 54, Jun. 15, 1994, pp. 3096–3100.

Ng et al., Inhibition of potentially lethal and sublethal damage repair by camptothecin and etoposide in human melanoma cell lines, Int. J. Radiat. Biol., vol. 66, No. 1, 1994, pp. 49–57.

Lamond et al., Radiation Lethality Enhancement With 9–Aminocamptothecin: Comparison To Other Topoisomerase I Inhibitors, Int. J. Radiation Oncology Biol. Phys. vol. 36, No. 2, 1996, pp. 369–376.

Lamond et al., The potential of topoisomerase I inhibitors in the treatement of CNS malignancies: report of a synergistic effect between topotecan and radiation, Journal of Neuro–Oncology 30, 1996, pp. 1–6.

Tamura et al., Enhancement of Tumor Radio–response by Irinotecan in Human Lung Tumor Xeongrafts, Jpn. J. Cancer Res. 88m, Feb. 1997, pp. 218–223.

Chen et al., Mammalian DNA Topoisomerase I Mediates the Enhancement of Radiation Cytotoxicity by Camptothecin Derivatives, Cancer Research 57, Apr. 15, 1997, pp. 1529–1536.

Kirichenko et al., Potentiation of Murine MCa–4 Carcinoma Radioresponse by 9–Amino–20(S)–camptothecin, Cancer Research 57, 1929–1933, May 15, 1997, pp. 1929–1933.

Omura et al., SN–38, a metabolite of the camptothecin derivative CPT–11, potentiates the cytotoxic effect of radiation in human colon adenocarcinoma cells grown as spheroids, Radiotherapy and Oncology 43, 1997, pp. 197–201.

(List continued on next page.)

Primary Examiner—Jerome D. Goldberg
(74) Attorney, Agent, or Firm—Wilson Sonsini Goodrich & Rosati

(57) ABSTRACT

Disclosed is a method of enhancing the therapeutic effect of radiation in a host being treated for cancer including coadministering the radiation and an orally dosed camptothecin derivative to the host being treated for cancer. Also disclosed is a method of enhancing the therapeutic effect of radiation in a host being treated for cancer including orally dosing the host being treated for cancer with a camptothecin derivative; and administering radiation at a point when a serum concentration of the camptothecin derivative in the host being treated for cancer reaches about 50% or more of the maximum concentration achieved by the oral dose.

15 Claims, No Drawings

OTHER PUBLICATIONS

Pantazis et al., Regression of Human Breast Carcinoma Tumors in Immunodeficient Mice Treated with 9–Nitro-camptothecin: Differential Response of Nontumorigenic and Tumorigenic Human Breast Cells in Vitro, pp. 1577–1582, Apr. 1, 1993.

Mattern et al., Synergistic Cell Killing by Ionizing Radiation and Topoisomerase I Inhibitor Topotecan (SK&F 104864), Nov. 1, 1991, pp. 5813–5816.

Punt et al., Phase 1 And Pharmacologic Study On The Topoisomerase 1 Inhibitor [PEG:1000] 99–Aminocamptothecin (9–AC) Given Orally To Patients (PTS) With Solid Tumors, Clinical Pharmacology, Proceedings of ASCO vol. 17, 1998.

Gerrits et al., Five Days of oral topotecan (Hycamtin), a phase I pharmacological study in adult patients with solid tumours, Eur. J. Cancer, vol. 34(7), Jun. 1998 pp. 1030–1035.

Gerrits et al., A comparison of clinical pharmacodynamics of different administration schedules of oral topotecan, Clin. Cancer Res., 5(1), Jan. 1999 pp. 69–75.

Drengler et al., Phase I and pharmacokinetic trial of oral irinotecan administered daily for 5 days every 3 weeks in patients with solid tumors, J. Clin. Oncol., 17(2), Feb. 1999, pp. 685–696.

Sauer, R. et al., "Topoisomerase–I–Inhibitor mit potentiell strahlensensibilisierender Wirkung", *Strahlentherapie und Onkologie*, vol. 173, No. 3, pp. 125–130, Mar. 1997, Abstract only.

Takimoto, C. et al. "Clinical applications of the camptothecins", *Biochimica et Biophysica Acta*, vol. 1400, No. 1–3, Oct. 1, 1998, pp. 107–119.

Takimoto, C. et al., "Clinical Status and Optimal Use of Topotecan", *Oncology*, vol. 11, No. 11, Nov. 1997, pp. 1635–1646.

Pantazis, P., "Preclinical studies of water–insoluble camptothecin congeners: cytotoxicity, development of resistance, and combination treatments", *Clin. Cancer Res.*, vol. 1, No. 11, Nov. 1995, pp. 1235–1244.

Rich, T. et al., "Camptothecin Radiation Sensitization: Mechanisms, Schedules, and Timing", *Oncology*, vol. 12, No. 8, Aug. 1998, pp. 114–120..

RADIOENHANCED CAMPTOTHECIN DERIVATIVE CANCER TREATMENTS

BACKGROUND OF THE INVENTION

1. Field of the Invention

This invention relates to chemotherapy and radiation therapy for treatment of cancers. More particularly, it relates to use of camptothecin derivatives as chemotherapeutic agents, together with radiation, for treatment of cancers.

2. Description of Related Art

The combination of chemotherapy and radiation therapy has become the treatment of choice for a number of cancers, particularly for advanced human malignancies. A number of chemotherapeutic drugs are known to be able to synergistically enhance the cytotoxicity of ionizing radiation. Widely-used chemotherapeutic agents, including 5-fluorouracil, etoposide, adriamycin, vinblastine, mitomycin C, cisplatin, bleomycin, and paclitaxel have all been shown to mediate radiosensitization effects via different mechanisms. Recently, improved clinical responses from chemoradiation have been obtained, and promising clinical protocols are being generated and tested in this exciting field of cancer treatment.

One repair mechanism of interest is DNA topoisomerase I. DNA topoisomerase I is a nuclear enzyme that is involved in catalyzing the interconversions of various topological states of DNA. The activity of DNA topoisomerase I is known to be important in many aspects of nucleic acid metabolism, such as DNA replication elongation, transcription elongation of RNA, and regulation of DNA supercoiling. Mammalian DNA topoisomerase I has been shown to be the cellular target of a number of anti-neoplastic compounds, including camptothecin and camptothecin derivatives.

20(S)-camptothecin (CPT), a plant alkaloid, was found to have anticancer activity in the late 1950's. Wall, M. et al., *Plant antitumor agents. I. The isolation and structure of camptothecin, a novel alkaloidal leukemia and tumor inhibitor from Camptotheca acuminata*, J. Am. Chem. Soc. 88: 3888–3890, (1966); Monroe E. Wall et al., *Camptothecin: Discovery to Clinic*, 803 Annals of the New York Academy of Sciences 1 (1996). These documents, and all documents (articles, patents, etc.) cited to herein, are incorporated by reference into the specification as if reproduced fully below. The chemical formula of CPT was determined to be $C_{20}H_{16}N_2O_4$.

Drug interference with the topoisomerase I-mediated breakage-rejoining of DNA strands is thought to be the common mechanism of drug action. Instead of direct inhibition of the catalytic activity of topoisomerase I, topoisomerase inhibiting drugs kill cells by converting an essential DNA topology modifying activity into a DNA breaking poison, which damages DNA through interactions with cellular processes such as replication of DNA. The presence of up-regulated, higher levels of topoisomerase I in both proliferating and quiescent tumor cells than in normal cells suggest that topoisomerase I-targeting drugs may possess a selected cytotoxic advantage against slow growing as well as rapidly proliferating tumors.

Camptothecin, whether substituted or unsubstituted, is believed to intervene in the mechanism of action of the nuclear enzyme topoisomerase I (topo I), arresting cells in the S phase. It is believed that CPT accomplishes this by stabilizing the covalently linked complexes of DNA-topo I (termed cleavable complexes), thus halting the progression of replication forks. This collision of the replication fork with the cleavable complexes is believed to trigger the apoptotic pathway. Z. Darzynkiewicz et al., *The Cell Cycle Effects of Camptothecin*, 803 Annals of the New York Academy of Sciences 93 (1996). DNA strand breaks are also implicated in the cytotoxic effects of CPT. F. Traganos et al., *Induction of Apoptosis by Camptothecin and Topotecan*, 803 Annals of the New York Academy of Sciences 101 (1996).

CPT itself is insoluble in water. However, during the sixties and seventies the sodium salt of CPT was derived from CPT through opening of the lactone ring using a mild base. Clinical trials were then conducted using this hydrosoluble, sodium salt derivative of CPT (CPT Na+), which was administered intravenously. The studies were later abandoned because of the high toxicity and low potency of CPT Na+. Gottlieb, J. A., et al., *Preliminary pharmacological and clinical evaluation of camptothecin sodium salt (NSC 100880)*, Cancer Chemother. Rep. 54:461–470 (1979); Muggia, F. M., et al., *Phase I clinical trials of weekly and daily treatment with camptothecin (NSC100880): Correlation with clinical studies*, Cancer Chemother. Rep. 56:515–521 (1972); Gottlieb, J. A. et al., *Treatment of malignant melanoma with camptothecin (NSC 100880)*, Cancer Chemother. Rep. 56:103–105 (1972); and Moertel, C. G., et al., *Phase II study of camptothecin (NSC 100880) in the treatment of advanced gastrointestinal cancer*, Cancer Chemother Rep. 56:95–101 (1972).

Despite its potential, interest in CPT as a therapeutic remained at a low ebb until the mid-1980's. By that time, drug therapies were being evaluated for treating human cancer using human cancer xenograft lines. During these evaluations, human tumors are serially heterotransplanted into immunodeficient, so-called "nude" mice, and the mice then tested for their responsiveness to a specific drug. (Giovanella, B. C., et al., *Cancer* 52(7): 1146 (1983)). The data obtained in these studies strongly support the validity of heterotransplanted human tumors into immunodeficient mammals, such as nude mice, as a predictive model for testing the effectiveness of anticancer agents.

Investigators began to experiment with various substituted forms of CPT. CPT and some of its substituted forms were found to be cytostatic for nontumorigenic cells and cytotoxic for tumorigenic cells; the selective toxicity of the compounds against tumorigenic cells in vitro and in vivo was an especially interesting feature of these drugs. Good activity was found when various substitutions were made to the CPT scaffold. For example, 9-Amino-20(S)-Camptothecin (9AC) and 10,11-Methylendioxy-20(S)-Camptothecin (10,11 MD) are capable of having high anticancer activity against human colon cancer xenografts. Giovanella, B. C., et al., *Highly effective topoisomerase-targeted chemotherapy of human colon cancer in xenografts*, Science 246:1046–1048 (1989).

Additionally, 9-nitrocamptothecin (9NC) has shown high activity against human tumor xenograft models. 9NC has a nine position hydrogen substituted with a nitro moiety. 9NC has inhibited the growth of human tumor xenografts in nude mice and has induced regression of human tumors established as xenografts in nude mice with little or no appearance of any measurable toxicity. D. Chatterjee et al., *Induction of Apoptosis in Malignant and Camptothecin-resistant Human Cells*, 803 Annals of the New York Academy of Sciences 143 (1996).

Other substituted CPT compounds that have shown promise include 7-ethyl-10-hydroxy CPT, and other 7, 9, 10, 11-substituted compounds.

The possibilities of combining radiation and CPT derivatives did not go unnoticed by researchers. Alexander V.

Kirichenko et al., *Potentiation of Murine MCa-4 Carcinoma Radioresponse by 9-Amino-20(S)-camptothecin*, Cancer Research 57:1929–1933 (1997); Allan Y. Chen et al., *Mammalian DNA Topoisomerase I Mediates the Enhancement of Radiation Cytotoxicity by Camptothecin Derivatives*, Cancer Res. 57:1529–1536 (1997); Kenji Tamura et al., *Enhancement of tumor Radio-response by Irinotecan in Human Lung Tumor Xenografts*, Jpn. J. Cancer Res. 88:218–223 (1997); John P. Lamond et al., *Radiation Lethality Enhancement with 9-Aminocamptothecin: Comparison to Other Topoisomerase I Inhibitors*, Int. J. Radiation Oncology Biol. Phys. 36:369–376 (1996); John P. Lamond et al., *The Potential of Topoisomerase I Inhibitors in the Treatment of CNS Malignancies: Report of a Synergistic Effect Between Topotecan and Radiation*, Journal of Neuro-Oncology 30:1–6 (1996); and Michael R. Mattern et al., *Synergistic Cell Killing by Ionizing Radiation and Topoisomerase I Inhibitor Topotecan (SK&F 104864)*, Cancer Research 51:5813–5816 (1991).

However, there remains a serious problem with respect to use of currently marketed CPT derivatives, such as topotecan (available as HYCAMPTIN from Smith-Kline Beecham) or irinotecan (available as CAMPTOSAR from Pharmacia & Upjohn), for use in chemoradiation therapies. This problem is that the currently marketed CPT derivatives are administered intravenously. Therefore, depending upon the labeled dosing schedule, it is quite possible that any given radiation regimen might call for radiation administration on a day when a patient might not be given CPT. For example, HYCAMPTIN may be administered to a patient for three days on and eleven days off, while a radiation therapy is typically may be administered for five days on, two days off. If so, then every other week the patient will not receive radiation while a CPT derivative is bioavailable in pharmacologically significant amounts.

There is therefore a need for methods whereby CPT derviatives may be administered together with radiation to overcome the problems mentioned above.

SUMMARY OF THE INVENTION

In one aspect, the invention relates to a method of enhancing the therapeutic effect of radiation in a host being treated for cancer including coadministering the radiation and an orally dosed camptothecin derivative to the host being treated for cancer. In another aspect, the invention relates to a method of enhancing the therapeutic effect of radiation in a host being treated for cancer including orally dosing the host being treated for cancer with a camptothecin derivative; and administering radiation at a point when a serum concentration of the camptothecin derivative in the host being treated for cancer reaches about 50% or more of the maximum concentration achieved by the oral dose.

DETAILED DESCRIPTION OF THE INVENTION

The inventors have unexpectedly discovered that it is possible to combine oral administration of CPT derivatives together with radiation therapy to arrive at a course of therapy wherein the CPT derviative is present in the circulatory system of a patient at the same time as radiation is administered. This coadministration helps to insure that inhibition of radiation repair is increased as compared to prior art courses of therapy.

Radiation may be administered according to the invention in a variety of fashions. For example, radiation may be electromagnetic or particulate in nature. Electromagnetic radiation useful in the practice of this invention includes, but is not limited to, x-rays and gamma rays. Particulate radiation useful in the practice of this invention includes, but is not limited to, electron beams, protons beams, neutron beams, alpha particles, and negative pi mesons. The radiation may be delivered using conventional radiological treatment apparatus and methods, and by intraoperative and stereotactic methods. Additional discussion regarding radiation treatments suitable for use in the practice of this invention may be found throughout Steven A. Leibel et al., *Textbook of Radiation Oncology* (1998) (publ. W. B. Saunders Company). Radiation may also be delivered by other methods such as targeted delivery, for example by radioactive "seeds," or by systemic delivery of targeted radioactive conjugates. Other conventional radiation delivery methods also may be used in the practice of this invention.

The amount of radiation delivered to the desired treatment volume may be variable. In a preferable embodiment, radiation may be administered in amount effective to cause the arrest or regression of the cancer in a host, when the radiation is coadministered with orally dosed camptothecin derivatives. More preferably, the amount of radiation dosed may be from about thirty to about seventy Gray; most preferably this amount of radiation is delivered by a standard linear accelerator. Most preferably this amount of radiation is delivered over about three to about seven weeks. The radiation administered in a variety of treatment plans, including, but not limited to, ranging from whole body to limited field. Choice of the radiation treatment plan may be made by one of skill in the art, depending upon the appropriate course of therapy.

Treatment plans may include, but are not limited to, opposed lateral fields, a wedge pair of fields, rotation or multiple field techniques. CT-guided treatment planning is suggested to improve accuracy in the selection of field arrangements. Isodose distributions for the initial treatment volume and the cone-down treatment volume are suggested for all patients, including those with parallel opposed fields. Composite plans showing dose distribution to the initial treatment volume and the boost treatment volume are desirable. The minimum and maximum dose to the treatment volume are preferably kept to within about 10% of the dose at the center of the treatment volume.

Another advantage of this invention occurs when radiation is administered according to a hyperfractionated radiation schedule. Under such a schedule, a patient may be radiated two or more times per day wherein the dose of radiation administered each time is a sub-fraction of the typical daily fraction of radiation normally administered. Use of oral camptothecin derivatives allows for patients undergoing hyperfractioned radiation therapy to have available therapeutically effective amounts of the camptothecin derivative during each of the individual treatments during the day. This is an advantage over typical IV treatments wherein a patient would need to receive IV infusions before and during each treatment, which would represent a significant burden on the patient in terms of safety and comfort.

Any orally bioavailable CPT derivatives with anti-cancer properties may be useful in the practice of this invention, particularly those with topoisomerase I inhibiting activity. Preferable CPT derivatives useful in the practice of this invention include, but are not limited to 9-nitrocamptothecin (available from SuperGen, San Ramon, CA), 9-aminocamptothecin (generally available from NCI), and topotecan (oral formulation may be available from Smith-Kline Beecham). Further information regarding these materials may be obtained from U.S. Pat. Nos. 5,225,404;

5,552,154; 5,652,244; 4,894,456; 4,981,968; 5,049,668; 5,053,512; 5,106,742; 5,122,526; 5,122,606; 5,180,722; 5,244,903; 5,227,380; 5,340,817; 5,364,858; 5,401,747; 5,496,830; 5,614,529; 5,646,159, all of which are incorporated by reference, as noted above. Punt, C. J. A. et al. *Phase I and Pharmacologic Study On The Topoisomerase 1 Inhibitor [PEG 1000] 9-Aminocamptothecin (9-AC) Given Orally To Patients (PTS) With Solid Tumors*, Proceedings of ASCO, Volume 17, 1998, Abstract 760.

In a preferable embodiment, camptothecin derivatives may be administered according to the invention in amounts effective to cause the arrest or regression of the cancer in a host, when the camptothecin derivatives are coadministered with radiation. More preferably, the camptothecin derivatives may be admnistered in amounts ranging from about one tenth of milligram per day to about one gram per day, even more preferably from about one tenth of a milligram per day to about ten milligrams per day, most preferably from about one milligram per day to about five milligrams per day. Dosing schedules may include five days on, two days off or four days on, three days off. More preferably, daily doses of the camptothecin derivative according to the invention are administered at least one out of every two days, still more preferably substantially every day that radiation is given to a host being treated for cancer.

The recited CPT derivatives may be administered by a variety of oral routes, and may be administered or coadministered in any conventional oral dosage form. Oral is defined in the context of this invention to include, but not be limited to dosage forms that may be inhaled, nasally administered or swallowed by a patient.

Coadministration in the context of this invention is defined to mean the administration of more than one therapeutic benefit in the course of a coordinated treatment to achieve an improved clinical outcome. Additionally, in coadministered therapy, in the context of this invention, the therapeutic benefits act on a patient in the coextensive fashion, that is, during overlapping periods of time. In a preferable embodiment, the coadministered therapy according to the invention is administered substantially completely coextensively. In such an embodiment, the overlap of the periods of time, during which the various therapeutic benefits act on the patient, is substantially complete. In another preferable embodiment, a camptothecin derivative according to the invention is orally dosed, and radiation is administered according to the invention at a point when the serum concentration of the camptothecin derivative reaches about 50% or more of the maximum concentration achieved by the oral dose.

A broad range of cancers may be treated using the present invention. These cancers comprise both primary and metastatic cancers. Specific types of cancers that can be treated using this invention include, but are not limited to, bladder, breast, cervical, cholangiocarcinoma, colorectal, gastric sarcoma, glioma, lung, lymphoma, melanoma, multiple myeloma, osteosarcoma, ovarian, pancreatic, prostate, stomach, cancers of the head and neck, or tumors at localized sites including inoperable tumors or in tumors where localized treatment of tumors would be beneficial, and solid tumors. In a more preferable embodiment, the types of cancer include pancreatic, and/or colorectal.

Additional preferable indications that may be treated using this invention include those involving undesirable or uncontrolled cell proliferation. Such indications include, but are not limited to, restenosis, insults to body tissue due to surgery, diseases that produce fibrosis of tissue, and disorders of tissues that are not highly vascularized. Specific types of restenotic lesions that can be treated using the present invention include coronary, carotid, and cerebral lesions. Treatment of cell proliferation due to insults to body tissue during surgery may be possible for a variety of surgical procedures, including joint surgery, bowel surgery, and cheloid scarring. Diseases that produce fibrotic tissue include emphysema. An example of cell proliferative disorders that may be treated using the invention is a bone tumor.

It will be apparent to those skilled in the art that various modifications and variations can be made in the methods of the present invention without departing from the spirit or scope of the invention. Thus, it is intended that the present invention cover the modifications and variations of this invention provided they come within the scope of the appended claims and their equivalents. Additionally, the following examples are appended for the purpose of illustrating the claimed invention, and should not be construed so as to limit the scope of the claimed invention.

EXAMPLES

Example 1

In vitro Experiment with 9-nitrocamptothecin

The radiation sensitizing of a novel, orally-administered camptothecin analog, 9-nitro-20(S)-camptothecin (RFS-2000, SuperGen, Inc.) was evaluated in vitro using the human H460 non-small cell lung carcinoma cell line. Cells were incubated with RFS-20 2000 for various times, irradiated with 137Cs gamma-rays during or before drug exposure, then colonies were formed.

The mean IC50 (inhibitory concentration at 50% survival) values for the RFS-2000 alone were 54 nM, 33 nM, and 10 nM for 1.5, 4, and 24 hr. incubations, respectively. For combination of RFS-2000 plus radiation, RFS-2000 doses of 5 nM, 10 nM and 15 nM were chosen which gave a S.F. value of 0.8, 0.5 and 0.15 with 24 hr incubation of drug alone, and radiation survival curves were normalized for this killing.

When cells were irradiated during a 1.5 hr drug treatment (at t=1 hr) or immediately after a 4 hr treatment, the effects of RFS-2000+radiation were additive. However, when cells were treated for 24 hr with RFS-2000 and then irradiated, a super-additive effect was observed. Using the 24 hr interval before irradiation, the radiation dose enhancement ratios (D.E.R.) calculated at a surviving fraction of 0.25 were 1.12, 1.4, and 2.2 for 5, 10 and 15 nM, respectively.

Example 2

A 47-year-ld male, presenting with pancreatic cancer, is administered three milligrams of 9-nitrocamptothecin orally, once per day for five days on, two days off. Four hours after administering the 9-nitrocamptothecin, the patient receives radiation in the amount of fifty Gray equally divided over five weeks, administered on a five days on, two days off schedule. This therapy continues for six weeks, until the total dose of radiation has been reached.

Example 3

A 47-year-old male, presenting with locally advanced non-small cell lung cancer, is administered three milligrams 9-aminocamptothecin orally, once per day for five days on, two days off. Four hours after administering the 9-aminocamptothecin, the patient receives radiation sixty Gray equally divided over six weeks on a five days on, two days off schedule. This therapy continues for three weeks, with a three week rest period before restarting therapy for another three weeks until the desired total dose of radiation has been reached.

Example 4

A 47-year-old male, presenting with rectal cancer, is administered 2 milligrams of 9-nitrocamptothecin orally, once per day for five days on, two days off. Four hours after administering the 9-nitrocamptothecin, the patient receives fifty Gray of radiation equally divided over five weeks on a five days on, two days off schedule. This therapy continues for six weeks, until the total dose of radiation has been reached.

What is claimed is:

1. A method for treating a cancer patient with a combination therapy, comprising:

administering x-ray radiation and orally dosed 9-nitrocamptothecin to a patient having a cancer sensitive to the combination therapy in a therapeutically effective amount, wherein the orally dosed 9-nitrocamptothecin is administered at least two hours before the x-ray radiation.

2. The method of claim 1, wherein the x-ray radiation is administered in amount effective to cause an arrest or regression of the cancer in the host.

3. The method of claim 1, wherein the x-ray radiation is administered in an amount ranging from about thirty to about seventy Gray.

4. The method of claim 1, wherein the x-ray radiation is delivered over about three to about seven weeks.

5. The method of claim 1, wherein the x-ray radiation is administered according to a hyperfractionated radiation schedule.

6. The method of claim 1, wherein the orally administered 9-nitrocamptothecin is administered in an amount effective to cause an arrest or regression of the cancer in the host.

7. The method of claim 1, wherein the orally administered 9-nitrocamptothecin is administered in an amount ranging from about one tenth of a milligram per day to about one gram per day.

8. The method of claim 1, wherein the orally administered 9-nitrocamptothecin is administered in an amount ranging from about one tenth of a milligram per day to about ten milligrams per day.

9. The method of claim 1, wherein the orally administered 9-nitrocamptothecin is administered in an amount ranging from about one milligram per day to about five milligrams per day.

10. The method of claim 1, wherein the 9-nitrocamptothecin is administered by an administration route selected from the group consisting of inhalation and nasal.

11. The method of claim 1, wherein the cancer comprises primary or metastatic cancers.

12. The method of claim 1, wherein the cancer is selected from the group consisting of cancers of a bladder, breast, cervical, cholangiocarcinoma, colorectal, gastric sarcoma, glioma, lung, lymphoma, melanoma, multiple myeloma, osteosarcoma, ovarian, pancreatic, prostate, stomach, cancers of a head and neck, and solid tumors.

13. The method of claim 1, wherein the cancer comprises pancreatic or colorectal cancer.

14. The method of claim 1, wherein doses of the 9-nitrocamptothecin is administered at least one out of every two days that the x-ray radiation is given to the host.

15. The method of claim 1, wherein the 9-nitrocamptothecin is administered substantially every day that x-ray radiation is given to the host.

* * * * *